United States Patent
Jackson et al.

[11] Patent Number: 5,916,678
[45] Date of Patent: Jun. 29, 1999

[54] WATER-DEGRADABLE MULTICOMPONENT FIBERS AND NONWOVENS

[75] Inventors: David Martin Jackson, Roswell, Ga.; William Seal Pomplun, Neenah; Pavneet Singh Mumick, Appleton, both of Wis.; Paul Windsor Estey, Cumming, Ga.

[73] Assignee: Kimberly-Clark Worldwide, Inc., Neenah, Wis.

[21] Appl. No.: 08/730,951

[22] Filed: Oct. 16, 1996

Related U.S. Application Data

[63] Continuation-in-part of application No. 08/497,667, Jun. 30, 1995, abandoned.

[51] Int. Cl.⁶ .............................. D02G 3/00; D04H 1/58
[52] U.S. Cl. .................. 428/373; 428/370; 428/374; 428/395; 442/361; 442/362; 442/363; 442/364; 442/394
[58] Field of Search ................... 428/373, 374, 428/370, 395; 442/361, 362, 363, 364, 394

[56] References Cited

U.S. PATENT DOCUMENTS

| D. 247,368 | 2/1978 | Whitehead | D24/51 |
|---|---|---|---|
| 3,276,944 | 10/1966 | Levy | 161/150 |
| 3,338,992 | 8/1967 | Kinney | 264/24 |
| 3,341,394 | 9/1967 | Kinney | 161/72 |
| 3,502,538 | 3/1970 | Petersen | 161/150 |
| 3,502,763 | 3/1970 | Hartmann | 264/210 |
| 3,542,615 | 11/1970 | Dobo et al. | 156/181 |
| 3,563,241 | 2/1971 | Evans et al. | 128/284 |
| 3,654,928 | 4/1972 | Duchane | 128/290 |
| 3,670,731 | 6/1972 | Harmon . | |
| 3,676,242 | 7/1972 | Prentice | 156/62.4 |
| 3,692,618 | 9/1972 | Dorschner et al. | 161/72 |
| 3,716,614 | 2/1973 | Okamoto et al. | 264/344 |
| 3,793,678 | 2/1974 | Appel | 19/156.3 |
| 3,802,817 | 4/1974 | Matsuki et al. | 425/66 |
| 3,849,241 | 11/1974 | Butin et al. | 161/169 |

(List continued on next page.)

FOREIGN PATENT DOCUMENTS

| 803714 | 1/1969 | Canada | 28/5 |
|---|---|---|---|
| 0080382A2 | 6/1983 | European Pat. Off. | D04H 1/56 |
| 0156160A2 | 10/1985 | European Pat. Off. | A61L 15/00 |
| 0 569 145 | 11/1993 | European Pat. Off. | D01F 6/70 |
| 0 648 871 | 4/1995 | European Pat. Off. | D01F 8/10 |
| 2513251A1 | 9/1976 | Germany | D01F 8/08 |
| 93 07199 | 4/1993 | WIPO | C08G 63/688 |

OTHER PUBLICATIONS

"Coform Engineered Composites" by Richard A. Anderson and Joseph D. Wahlquist, Nonwovens World, Nov. 1986.
"A Simple Test for Dispersion of Wet Chop Fiberglass in Water," 1996 TAPPI Proceedings Nonwovens Conference.
Database WPI, Section Ch, Week 9418, Derwent Publications Ltd., London, GB; Class A23, AN 94–148344 XP002017458 & JP,A, 06 093 516 (Kuraray Co Ltd), Apr. 5, 1994, See Abstract.

(List continued on next page.)

Primary Examiner—William Krynski
Assistant Examiner—J. M. Gray
Attorney, Agent, or Firm—Nicholas N. Leach; James B. Robinson

[57] ABSTRACT

Disclosed herein are multicomponent fibers wherein at least one component will permit bonding of the fibers to themselves and other types of fibers and wherein the same first component is also degradable in an aqueous medium. Such fibers can be used to form fibrous nonwoven webs which can be used as components in such end-use products as medical and health care related items, wipes and personal care absorbent articles.

17 Claims, 3 Drawing Sheets

5,916,678

U.S. PATENT DOCUMENTS

| | | | |
|---|---|---|---|
| 3,881,490 | 5/1975 | Whitehead et al. | 128/287 |
| 3,971,373 | 7/1976 | Braun | 128/146.2 |
| 4,002,171 | 1/1977 | Taft | 128/284 |
| 4,100,324 | 7/1978 | Anderson et al. | 428/288 |
| 4,340,563 | 7/1982 | Appel et al. | 264/518 |
| 4,381,335 | 4/1983 | Okamoto | 428/373 |
| 4,419,403 | 12/1983 | Varona | 428/288 |
| 4,429,001 | 1/1984 | Kolpin et al. | 428/283 |
| 4,496,619 | 1/1985 | Okamoto | 428/373 |
| 4,604,313 | 8/1986 | McFarland et al. | 428/172 |
| 4,627,950 | 12/1986 | Matsui et al. | 264/103 |
| 4,789,592 | 12/1988 | Taniguchi et al. | 428/373 |
| 4,795,668 | 1/1989 | Krueger et al. | 428/174 |
| 4,902,559 | 2/1990 | Eschwey et al. | 428/224 |
| 4,966,808 | 10/1990 | Kawano | 428/373 |
| 5,057,368 | 10/1991 | Largman et al. | 428/397 |
| 5,069,970 | 12/1991 | Largman et al. | 428/373 |
| 5,102,668 | 4/1992 | Eichel et al. | 424/490 |
| 5,108,820 | 4/1992 | Kaneko et al. | 428/198 |
| 5,277,976 | 1/1994 | Hogle et al. | 428/397 |
| 5,290,626 | 3/1994 | Nishio et al. | 428/224 |
| 5,304,420 | 4/1994 | Hirakawa et al. | 428/373 |
| 5,336,552 | 8/1994 | Strack et al. | 428/224 |
| 5,350,624 | 9/1994 | Georger et al. | 428/219 |
| 5,366,804 | 11/1994 | Dugan | 428/373 |
| 5,382,400 | 1/1995 | Pike et al. | 264/168 |
| 5,407,442 | 4/1995 | Karapasha | 604/359 |
| 5,466,410 | 11/1995 | Hills | 264/172.11 |

OTHER PUBLICATIONS

Database WPI, Section Ch, Week 9320, Derwent Publications Ltd., London, GB; Class A23, AN 93–162362 XP002017459 & JP,A,05 093 318 (Unitika Ltd), Apr. 16, 1993, See Abstract.

Database WPI, Section Ch, Week 9434, Derwent Publications Ltd., London, GB; Class A96, AN 94–276136 XP002017460 & JP,A,06 207 324 (Unitika Ltd), Jul. 26, 1994, See Abstract.

Database WPI, Section Ch, Week 9529, Derwent Publications Ltd., London, GB; Class A23, AN 95–220948 XP002017461 & JP,A,07 133 511 (Toyobo KK), May 23, 1995, See Abstract.

Database WPI, Section Ch, Week 9511, Derwent Publications Ltd., London, GB; Class A81, AN 95–078519 XP002017462 & JP,A, 07 003 600 (Daiwabo Co Ltd), Jan. 6, 1995, See Abstract.

Patent Abstracts of Japan, vol. 014, No. 017 (C–675), Jan. 16, 1990 & JP,A,01 260017 (Toray Ind Inc), Oct. 17, 1989, See Abstract.

WATER-DEGRADABLE MULTICOMPONENT FIBERS AND NONWOVENS

This application is a continuation-in-part of application Ser. No. 08/497,667, entitled "Water-Degradable Multicomponent Fibers and Nonwovens" and filed in the U.S. Patent and Trademark Office on Jun. 30, 1995 now abandoned. The entirety of this application is hereby incorporated by reference.

FIELD OF THE INVENTION

The present invention is directed to multicomponent fibers. More particularly, the present invention is directed to multicomponent fibers including bicomponent fibers which have at least one component which will permit bonding of the fibers to themselves and other types of fibers and wherein the same component is also degradable in an aqueous medium. Such fibers can be used to form fibrous nonwoven webs and can be used as components in such end products including, but not limited to, medical and health care related items, wipes and personal care absorbent articles such as diapers, training pants, incontinence garments, sanitary napkins, bandages and the like.

BACKGROUND OF THE INVENTION

Solid waste disposal is becoming an ever increasing problem throughout the world. As landfills continue to fill up, there has been an increased demand for material source reduction in disposable products, the incorporation of more recyclable components in disposable products and the design of products which can be disposed of by means other than by incorporation into solid waste disposal facilities such as landfills.

One product area that has received particular attention with respect to solid waste disposal is disposable diapers. Most diapers in the United States are disposed of in landfills. Other proposed methods of disposal have included making all or a portion of the diapers flushable in public sewage systems and/or making their components more compatible with evolving composting and biomethanization techniques.

Diapers and almost all personal care products include in their design a bodyside cover, an absorbent core and some type of outercover to protect the clothing of the wearer from becoming soiled. Most bodyside covers and outercovers are made from fibrous nonwoven webs and/or films that are made from thermoplastic polymers such as polyolefins and polyesters. These portions of the product and especially diapers usually have to have a fairly high degree of integrity so that they remain intact during use. This same integrity, however, makes their disposal as, for example, through flushing in a toilet just that much more difficult. Consequently there is a need for materials, components and product designs which make such disposable items as personal care absorbent products more compatible with alternative disposal techniques such as toilet flushing, composting and biomethanization.

SUMMARY OF THE INVENTION

The present invention is directed to a multicomponent fiber which includes a first component, at least a second component and optionally more components if so desired. The first component forms an exposed surface on at least a portion of the fiber. This first component is water-degradable and may be made from a wide variety of water-degradable polymers including, for example, poly (vinyl alcohol) and sulfonated polyester. The second component may be made from a thermoplastic fiber-forming polymer which is capable of being extruded through, for example, bicomponent fiber-forming equipment. Examples of such polymers include, but are not limited to, polyolefins and polyesters. If desired, the second component also can be made from a polymer which is water-degradable though it generally will be more advantageous if the second polymer degrades at a rate which is slower than the degradation rate of the first component. Multicomponent fibers such as bicomponent fibers may be extruded in a number of forms including, but not limited to, concentric and eccentric sheath/core configurations and side-by-side configurations. If desired, additional components also may be incorporated into the multicomponent fibers according to the present invention including other polymers and/or additives.

In a specific embodiment of the present invention, the first component is a thermally or heat bondable polymer. The first component remains stable in the presence of a trigger component, such as,, for example, the sulfate ion or chloride ion, at concentration levels found in body fluids, such as urine, yet disperses or disintegrates in a period not exceeding 30 minutes in the presence of such trigger component at concentration levels found in normal tap water, such as is used in conventional toilet disposal. Suitable examples of such first component include water-dispersible polyester or polyamide polymers or copolymers. The second component may be made from a thermoplastic fiber-forming polymer that is capable of being extruded through, for example, bicomponent fiber-forming equipment.

The multicomponent fibers according to the present invention may be used to form fibrous nonwoven webs using heat and/or pressure to bond the fibers together using the first component as the bonding agent. The webs may be formed completely from fibers according to the present invention or they may be blended with other fibers. Once the webs have been formed they may be used to form all or a portion of a number of end-use products including, but not limited to, personal care absorbent articles.

DETAILED DESCRIPTION OF THE INVENTION

The present invention is directed to a multicomponent fibers such as bicomponent fiber which includes a first component and a second component. For purposes of illustration only, the present invention will be described relative to a bicomponent fiber. It should be understood, however, that the scope of the invention is meant to encompass fibers with two or more components and thus "multicomponent"

fibers. The first component provides at least two functions. First, it provides an exposed portion on the surface of the bicomponent fiber which will permit thermal bonding of the fiber to other fibers which may be the same as or different from the fibers of the present invention. Second, the first component of the bicomponent fiber of the present invention must be degradable when placed in an aqueous medium. As a result, the bicomponent fiber of the present invention can be used to form thermally bonded fibrous nonwoven webs. Then, when the web is exposed to an aqueous medium such as water in a toilet bowl, the fiber-to-fiber bond caused by the first component will degrade to a sufficient degree so that the fiber-to-fiber bonds will break apart thereby causing the fibrous nonwoven web to lose its integrity and break apart into smaller pieces or into individual fibers.

The second component is another fiber forming polymer which is less degradable in an aqueous medium when compared to the first component or totally non-degradable. Generally, the purpose of the second component will be to provide rigidity to the fiber and thus the resultant nonwoven web.

Figure 1:
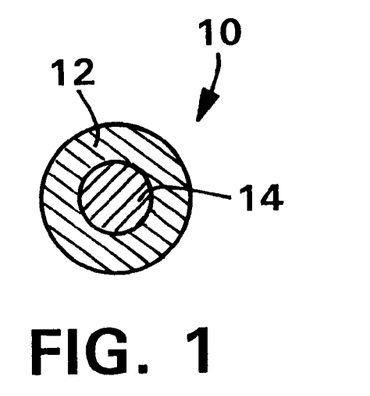
FIG. 1 is a cross-sectional view of a concentric sheath/core bicomponent fiber according to the present invention.
Figure 2:
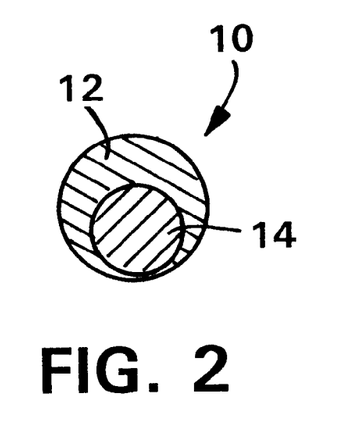
FIG. 2 is a cross-sectional view of an eccentric sheath/core bicomponent fiber according to the present invention.
Figure 3:
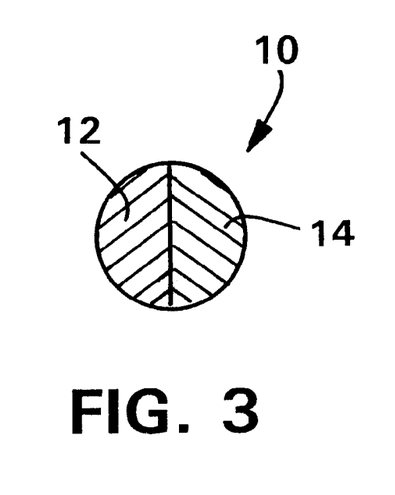
FIG. 3 is a cross-sectional view of a side-by-side bicomponent fiber according to the present invention.

Referring to FIGS. 1 through 3, the bicomponent fibers 110 according to the present invention will have two or more components including a first component 12 and a second component 14 with the first component being "water-degradable". By this it is meant that when the first component 12 of the bicomponent fiber 10 is exposed to an aqueous liquid, including plain water such as is found in a toilet bowl or an aqueous mixture which may have added buffer, alkaline or acidic components or complex formers, the bond formed between the fibers by the first component will sufficiently weaken such that the fibers will begin to break apart by themselves or if necessary with agitation. To effect bonding, the first component 12 has a melting or softening temperature lower than the melting or softening temperature of the second component. In addition, as shown by FIGS. 1 through 3, the first component forms at least a portion of the exposed surface of the fiber 10, usually along the longitudinal axis of the fiber 10. Fiber cross-sections which provide such an exposed surface for the first component include, but are not limited to, a concentric sheath/core configuration such as is shown in FIG. 1, an eccentric sheath/core configuration such as is shown in FIG. 2 and a side-by-side configuration such as is shown in FIG. 3. As a result, the first component serves as the bonding means for bonding the fibers together while the second component provides the structural rigidity to the fiber and the resultant nonwoven web.

The second component 14 is a polymer which has a higher melting or softening temperature than the first component 12 so that when thermal bonding is used to bond the bicomponent fibers together, the first component 12 is the primary means for effecting interfiber bonding. To accomplish this, it is generally desirable that the second component have a melting/softening temperature which is at least 10° C. greater than the melting/softening temperature of the first component 12. Polymer or polymer blends which are relatively crystalline in nature will either have a specific melting temperature or a very narrow melting temperature range. Other polymers are more amorphous and thus will melt or soften over a broader temperature range. For polymers which are relatively crystalline, the melting temperature can be determined using differential scanning calorimetry (DSC) pursuant to ASTM Test Method E-794-85. For polymers which are more amorphous, the softening temperature or temperature range for the particular polymer, copolymer or blend can be determined using ASTM (Vicat) Test Method D1525 (1993). Thus when choosing polymers for making the first and second components, the highest end of the melting or softening temperature range of the first component 12 should be at least 10° C. lower than the lowest end of the melting or softening temperature range for the second component 14. As a result, when bonding of the bicomponent fibers is undertaken, the majority of the interfiber bonds will be via the first component and not the second component, provided the bonding temperature/conditions do not fall into the melting temperature range of the second component. Examples of polymers which are commonly used as the core or second component include, but are not limited to, polyesters and polyolefins such as polyethylene and polypropylene. Another factor in selecting the second component 14, is that it be sufficiently compatible with the first component from an adhesion standpoint so that the two components do not unduly separate from one another once the fiber 10 has been formed. This is especially true with respect to a side-by-side fiber configuration where there is little or no encapsulation of one component by the other as is the case with eccentric and concentric sheath/core fiber configurations.

Typically the material chosen to form the first component 12 will be more expensive than the second component 14. As a result, it is generally desirable to use as little of the first component when forming the fiber as is possible to reduce costs. To further reduce costs, it may be desirable to use other, lower cost fibers within the fibrous nonwoven web incorporating bicomponent fibers according to the present invention. Consequently, when mixing fibers, the fibers should be selected such that the first component of the bicomponent fiber according to the present invention will have the lowest melting/softening point of all of the fiber polymers being used in the nonwoven web.

As mentioned previously, the first component must be a material which is thermally bondable so as to be able to form fibrous nonwoven webs. The first component must also be water-degradable as outlined previously. Many polymers are degradable in essentially plain water such as tap water which typically has a pH in the range of about 6.5 to about 8.5. Thus, if fibrous nonwoven webs are made using water-degradable bicomponent fibers according to the present invention, then they will most likely be suitable for uses where they are exposed to very little or no water. Then, after use, they can be placed in water so that the sheaths can degrade and the fibrous nonwoven web can break apart. In other applications, fibrous nonwoven webs using water-degradable bicomponent fibers according to the present invention may be exposed to sufficient quantities of aqueous liquids during use, such that the first component would begin to degrade and break apart prematurely. Personal care absorbent articles such as diapers, incontinence garments, training pants and wet wipes are examples of such products which may be subject to this problem. To solve or reduce this problem, polymers can be selected for the first component which are sensitive to or become degradable as a result of pH change, dissolved ion concentration change and/or temperature change in the aqueous environment.

As described in further detail below, certain first component polymers are water-degradable only when exposed to sufficient quantities of water within a certain pH range. Outside this range, they will not degrade. Thus it is possible to choose a pH-sensitive first component polymer which will be non-degradable in an aqueous liquid or liquids in one pH range, for example a pH of 3 to 5, but which become degradable in the pH range of normal tap water. See for example U.S. Pat. No. 5,102,668 to Eichel et al. which is incorporated herein by reference in its entirety.

Another mechanism which can be used to trigger water-degradability is ion sensitivity, where the term "ion" is given its conventional meaning of an atom or molecularly bonded group of atoms, which has gained or lost one or more electrons and consequently has a negative or positive electrical charge. Certain polymers contain acid-based (R—COO$^-$) components which are held together by hydrogen bonding. In a dry state, these polymers remain solid. In an aqueous solution which has a relatively high ion concentration, such as urine, the polymer still will remain relatively intact. However, when the same polymer is later exposed to larger quantities of water with reduced ion content, such as can be found in a toilet bowl, the ion concentration will decrease and the hydrogen bonding will begin to break apart. As this happens, the polymer, itself, will begin to break apart in the water. See for example, U.S. Pat. No. 4,419,403 to Varona which is incorporated herein by reference in its entirety.

Yet another means for rendering a polymer degradable in water is through the use of temperature change. Certain polymers exhibit a cloud point. As a result, these polymers will precipitate out of solution at a particular temperature the cloud point. These polymers can be used to form fibers which are insoluble in water above a certain temperature but which become soluble and thus degradable in water at a lower temperature. As a result, it is possible to select or blend a polymer which will not degrade in body fluids, such as urine, at or near body temperature (37° C.) but which will degrade when placed in water at temperatures at or below room temperature (23° C). An example of such a polymer is polyvinylmethylether which has a cloud point of 34° C. When this polymer is exposed to body fluids such as urine at 37° C., it will not degrade as this temperature is above its cloud point (34° C). However, if the polymer is placed in water at room temperature (23° C.), the polymer will go back into solution as it is now exposed to water at a temperature below its cloud point. Consequently, the polymer will begin to degrade.

First component polymers can be categorized according to the means by which they are found to be stable in specific fluid environments. These environmental conditions are: low volume water or body fluids, regulated pH conditions (such as found in wet-wipe storage solutions or buffered systems), high ionic strength solutions (for example, baby or adult urine and menses), and variable temperature conditions (for example, body temperature versus room temperature or colder tap water).

Referring to Table I, examples of first component polymers that are stable in low water volume solution environments (for example, panti-liners, light incontinence products and baby or adult wipes), could be NP2068, NP2074 or NP2120 polyamides as supplied by the H. B. Fuller Company of Vadnais Heights, Minn. The Fuller materials are aliphatic polyamides which are completely cold water soluble and process in fiber spinning very similarly to low density polyethylene. Other polymers capable of degrading in aqueous mixtures or toilet water are poly (vinyl alcohol) graft copolymers supplied by the Nippon Synthetic Chemical Co., Ltd., Osaka, Japan, coded Ecomaty AX2000, AX10000 and AX300G. The Nippon polymers are cold water soluble but somewhat slower in their rate of solubility than the Fuller polymers. Yet another first component polymer could be a polyether blockamide, coded PEBAX® MX1074, supplied by Atochem (USA) located in Philadelphia, Pa. The PEBAX® MX1074 polymer is composed of epsilon-caprolactam (Nylon 12) and tetramethylene glycol monomers. These monomers are polymerized to make a series of a polyether block amide copolymers. The PEBAX® polymer is not water soluble but is water-swellable, and therefore could also be used in a higher water volume environment as well. The Fuller polymers can be matched to a second component (core) polymer with a softening or melting temperature at least about 10° C. higher, such as would be the case with polypropylene. The Nippon or Atochem polymers can be matched with a higher melting temperature range second component polymer such as polypropylene or poly (butylene terephthalate).

TABLE I

SHEATH POLYMERS FOR BICOMPONENT FIBERS

| Polymer Type | Melt Flow* Or Viscosity | DSC Soft Temp (Range) | Matched Core Polymer |
|---|---|---|---|
| H.B. Fuller Code NP-2120 | 410 Pa · s @ 204° C. | 142° C.–158° C. | Polypropylene |
| H.B. Fuller Code NP-2068 | 95 Pa · s @ 204° C. | 128° C.–145° C. | Polypropylene |
| H.B. Fuller Code NP-2074 | 290 Pa · s @ 204° C. | 133° C.–145° C. | Polypropylene |
| ATOCHEM PEBA ® MX1074 | MFR = 1–3 | 158° C. | Polybutyl-terephthalate |
| Nippon-Gohsei ECOMATY AX10000 | MFR = 100 | 180° C. | Polybutyl-terephthalate |
| Findley Blend N-10, Acylate ester/acrylic or methacrylic acid | 200 Pa · s @ 140° C. | 117° C. | Polyethylene |
| Findley Blend H-10, Acrylate ester/acrylic or methacrylic acid | 370 Pa · s @ 160° C. | 131° C. | Polypropylene |
| Findley Blend X-10, Acrylate ester/acrylic or methacrylic acid | 30 Pa · s @ 190° C. | — | — |
| Eastman Code AQ38S | 300 Pa · s @ 200° C. | 120° C.–130° C. | Polyethylene |
| National Starch Code 70-4442 | 40 Pa · s @ 180° C. | 80° C.–100° C. | Polypropylene or Polyethylene |
| National Starch Code 70-4395 | 22 Pa · s @ 180° C. | 80° C.–100° C. | Polypropylene or Polyethylene |

*ASTMD Test Method D-1238-906 (2.16 kg load at 190° C. for polyethylene)

First component polymers that are stable in a specific pH range, as for example, from pH 35 could be acrylate ester/acrylic or methacrylic acid copolymers and blends coded N-10, H-10 or X-10 as supplied by Findley Adhesives, Inc. of Milwaukee, Wis. The Findley materials are stable at body pH conditions (or when buffered against body fluids), but will break-up rapidly in toilet water during the flushing process (excess water) thus increasing the pH towards neutral. The Findley polymers can be matched with a higher melting temperature range second component polymer such as polyethylene or polypropylene.

First component polymers that are stable in high ion concentration solution environments (for example, baby or adult urine and menses) could be sulfonated polyesters coded AQ29, AQ38, or AQ55, as supplied by the Eastman Chemical Company of Kingsport, Tenn. The Eastman AQ38 polymer is composed of 89 mole percent isophthalic acid, 11 mole percent sodium sulfoisophthalic acid, 78 mole percent diethylene glycol and 22 mole percent 1,4-cydohexanedimethanol. It has a nominal molecular weight of 14,000 Daltons, an acid number less than two, a hydroxyl number less than 10 and a glass transition temperature of 38°

C. Other examples could be blends of poly(vinyl alcohol) or copolymers of poly(vinyl alcohol) blended with polyacrylic or methacrylic acid, or polyvinyimethyl ether blended with polyacrylic or methacrylic acid. The Eastman polymers are stable in high ionic solution environments, but will break-up rapidly in toilet water during the flushing process (excess water) thus reducing ion concentration. The Eastman polymers can be matched with a higher melting temperature range second component polymer such as polyethylene.

Other first component polymers that are stable in high ion concentrations include "triggered, water-dispersible polymers." By this it is meant that when the first component 12 of the bicomponent fiber 10 is exposed to a trigger component, such as, for example, the sulfate ion or chloride ion, at a first concentration level found in normal tap water, the polymer forming the first component disperses or disintegrates in no more than 30 minutes. However, when the first component 12 of bicomponent fiber 10 is exposed to the same trigger component at a second, higher concentration level typically found in body fluids, such as infant or adult urine, the polymer forming the first component remains stable and does not disperse. For example, Suitable examples of such first component include water-dispersible polyester or polyamide polymers, or copolymers, such as copolyester polymers available from National Starch and Chemical Company under the product designations 70-4395 and 70-4442. The inventors of the subject invention have discovered that multicomponent fibers, such as bicomponent fibers, having a first component comprising a triggered, water-dispersible polymer are insensitive to the presence of a particular trigger component at a concentration level found in urine, yet are highly sensitive to and disperse in a period not exceeding 30 minutes in the presence of the same trigger component at a different, lower concentration level typically found in excess tap water, such as is found in toilet bowls. Thus, fibrous nonwoven webs formed from or incorporating the multicomponent fibers of the present invention are unaffected in terms of dispersibility when insulted with body fluids, such as urine, yet when disposed of in normal tap water tend to break apart as the first component of the multicomponent fibers disperses.

First component polymers that are stable at body temperature conditions (that is a temperature of 37° C.) could be any polymer that exhibits a "cloud point" at or near body temperature. The cloud point, or inverse solubility temperature is a useful property for "triggering" a change in physical state, such as water solubility. For example, polyvinylmethylether has a cloud point temperature of 34° C. above which it is no longer water soluble, but at room temperature (near 23° C.) it is completely water degradable. Blends of polyvinylmethylether may be considered as well. Polyvinylmethylether can be matched with higher melting temperature range second component polymers such as polyethylene.

The methods for making bicomponent fibers are well known and need not be described herein in detail. To form a bicomponent fiber, generally, two polymers are extruded separately and fed to a polymer distribution system where the polymers are introduced into a segmented spinneret plate. The polymers follow separate paths to the fiber spinneret and are combined in a spinneret hole which comprises either two concentric circular holes thus providing a sheath/core type fiber or a circular spinneret hole divided along a diameter into two parts to provide a side-by-side type fiber. The combined polymer filament is then cooled, solidified and drawn, generally by a mechanical rolls system, to an intermediate filament diameter and collected. Subsequently, the filament is "cold drawn", at a temperature below its softening temperature, to the desired finished fiber diameter and is crimped/texturized and cut into a desirable fiber length. Bicomponent fibers can be cut into relatively short lengths, such as staple fibers which generally have lengths in the range of 25 to 51 millimeters (mm) and short-cut fibers which are even shorter and generally have lengths less than 18 millimeters. See, for example, U.S. Pat. No. 4,789,592 to Taniguchi et al. and U.S. Pat. No. 5,336,552 to Strack et al, both of which are incorporated herein by reference in their entirety.

Fibrous nonwoven webs may be made completely from the fibers of the present invention or they may be blended with other fibers. The length of the fibers will depend upon the particular end use. Where the fibers are to be degraded in water, for example, in a toilet, it is advantageous if the fiber lengths are maintained at or below about 15 millimeters (mm). Fibers having lengths of 15 mm or less do not tend to form ropes capable of causing plugs in home sewage systems or treatment plants, which can become a nuisance to the home owner or sewage treatment operator.

Although various nonwoven web manufacturing processes, such as spunbond processes, can be employed in forming nonwoven webs incorporating the water-dispersible bicomponent fibers of the present invention, dry (air-laid) processes can be suitably employed when working with short-cut staple fibers (15 mm or less in length) in order to achieve three dimensional bulk and good tactile properties, which can be beneficial in personal care product applications. Typically, for an air-laid nonwoven coverstock or bodyside liner, a blend of staple fibers (not exceeding 15 mm in length) would be used to achieve an acceptable material composed of, for example, polypropylene staple fibers and bicomponent (concentric or non-concentric) binder fibers. The bicomponent binder fibers would typically form from about 25% to about 100% by weight of the total weight of the nonwoven web being formed, with polypropylene (or other synthetic or natural) fibers forming the remaining 0% to about 75%. Basis weights for such coverstock webs can range from about 15 to about 30 grams per square meter (gsm), while basis weights for surge management layers can range from about 50 to about 200 gsm. In addition, surge materials can include stiffer fibers, for example, polyethylene terephthalate, having fiber sizes in the range of 6-10 denier. Typically, the fiber size of the water-dispersible bicomponent fibers of the present invention will range from about 1 to about 6 denier.

The water-degradable bicomponent fibers of the present invention may be used to form fibrous nonwoven webs for a number of uses. As a result, the examples listed herein should not be construed as a limitation as to the scope of the present invention.

Personal care absorbent articles include such items as diapers, training pants, feminine hygiene products such as sanitary napkins, panti-liners and tampons, incontinence garments and devices, bandages and the like. The most basic design of all such articles typically includes a bodyside liner, an outercover and an absorbent core disposed between the bodyside liner and the outercover. Generally, the bodyside liner and the outercover are sealed about their peripheries so as to encapsulate the absorbent core and thus make it possible to entrap and retain any fluids contained within the absorbent core. Depending upon the design of the particular personal care absorbent article, other components also may be included. Thus, the product may include such things as elastic side panels, fluid containment flaps, fastening devices and other layers of fluid transfer or retention materials. Where suitable, fibrous nonwoven webs incorporating such water-degradable bicomponent fibers may be used to form all or a portion of the foregoing components.

Other potential uses for the fibers and nonwoven webs according to the present invention include, but are not limited to, wet and dry wipers, articles of clothing and any other nonwovens or composites where a water-degradable feature might be advantageous.

Having thus described the various parameters of the present invention, several samples of the water-degradable bicomponent fibers and nonwoven webs were made.

EXAMPLE I

In Example I a sheath/core water-degradable bicomponent fiber was made using a high density polyethylene core and a sulfonated polyester sheath in a 50/50 weight ratio. The core polymer was NCPE 1961 high density polyethylene from Neste Oy, of Espoo, Finland with a melting temperature range of 140–150° C. The sheath polymer was AQ38S sulfonated polyester from the Eastman Chemical Company of Kingsport, Tenn. with a melting temperature range of 120–130° C. The fibers were produced utilizing a bicomponent fiber line, at an initial fiber diameter of 6 decitex (dtex) and were then cold drawn at a draw temperature of between 50 and 60° C. to a final diameter of 4 dtex. The fibers were mechanically crimped in a stuffer box and cut to a length of 6 mm. A neat iso-propyl myristate spin finish was also used.

Once the fibers had been formed, they were then air laid in a 50/50 weight ratio, based upon the total weight of the web, the fibrous nonwoven web having a basis weight of 25 to 30 grams per square meter (gsm) in combination with one of three other 1.7 dtex by 6 mm fibers. The three other fibers included a polyester fiber from the Dupont Fiber Company of Wilmington, Delaware, a polyester fiber from EMS Grilon of Domat/Ems, Switzerland and a rayon fiber from Courtaulds, Ltd. of Coventry, England. All three webs were bonded using a two step bonding process. In the first step for the blended rayon/water-degradable bicomponent fiber web, the fibers were through-air bonded at a temperature of 132° C. followed by point bonding in a pair of patterned bonding rolls with a bond area of about 15 percent at a temperature of 90° C. The blended polyester/water-degradable fiber webs were bonded at the same temperatures but bonding of the web containing the Dupont polyester fibers could not be perfected due to excessive shrinking of the polyester fibers. The fibers of the other two webs that did bond, formed fiber-to-fiber bonds via the sulfonated polyester sheath component. When the webs were placed in room temperature water and agitated, the fiber bonds degraded and the webs broke apart.

EXAMPLE II

In Example II, a second sheath/core water-degradable fiber was formed using a core made from VESTODUR® 1000 poly(butylene terephthalate) polymer from Hulls, GmbH a subsidiary of Veba AG of Duesseldorf, Germany. The PBT polymer had a melting temperature of 250° C. The water-degradable sheath was made from AX2000 poly(vinyl alcohol) from Nippon Synthetic Chemical Company, Ltd. of Osaka, Japan. It had a melting temperature of 225° C. As with the fibers in Example I, the sheath/core polymer weight ratio was 50/50. The fibers were initially drawn to 14 dtex and then cold drawn to 5 dtex at a temperature of 130° C. Following formation, the fibers were mechanically crimped and cut to a length of 6 mm. The same iso-propyl myristate spin finish was used on the fibers.

The water-degradable sheath/core bicomponent fibers were again blended with the same Ems Grilon polyester fibers and Courtaulds rayon fibers used in Example I in a 50/50 weight percent blend of polyester and bicomponent fibers and rayon/bicomponent fibers. The two air laid webs had basis weights of between 25 and 30 gsm. Bonding of the two webs was unsuccessful due to equipment limitations. Despite this, the poly(vinyl alcohol) sheaths of the bicomponent fibers did degrade and became slimy when placed in water.

EXAMPLE III

In Example III, film samples formed from National Starch 70-4442 polymer were made using a polymer film pressing accessory and Carver Press (see FIGS. 4 and 5), then tensile tests were performed. The film pressing accessory include a fixed female lower platen and a male upper platen, both of which were electrically heated and water-cooled. The depth of the lower platen was controlled by placing shims of 0.03302 centimeter (cm) thickness on both support arms of the film pressing accessory.

Figure 4:
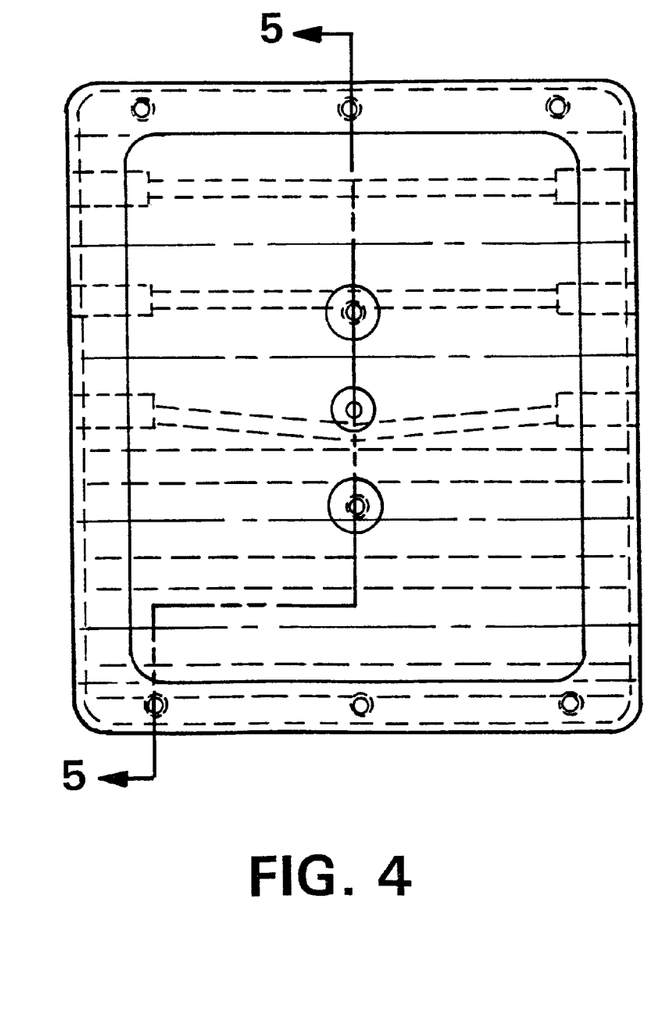
FIG. 4 is a plan view of the upper platen of a film pressing accessory used in forming polymer film samples.
Figure 5:
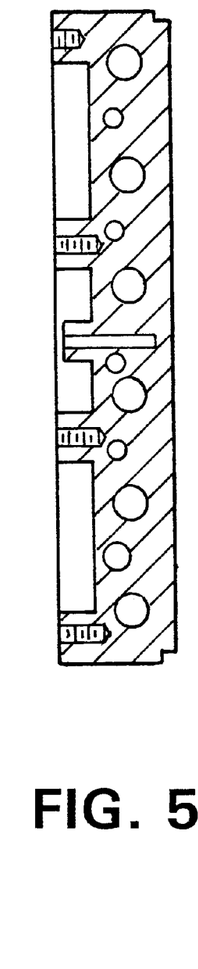
FIG. 5 is a cross-sectional view of the upper platen of FIG. 4.
Figure 6:
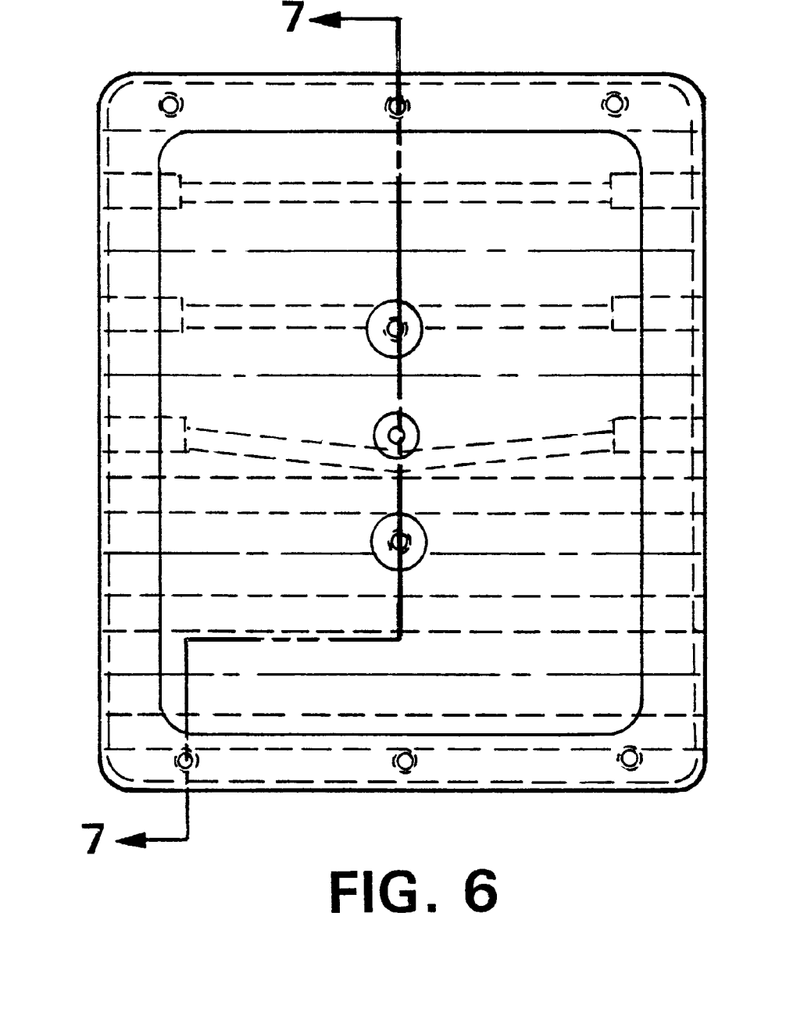
FIG. 6 is a plan view of the lower platen of the film pressing accessory used in forming polymer film samples.
Figure 7:
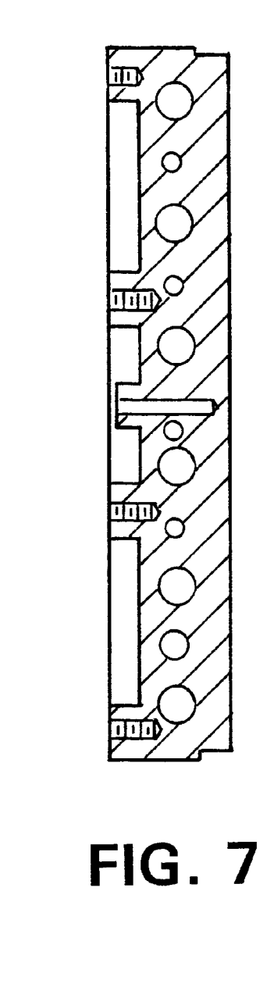
FIG. 7 is a cross-sectional view of the lower platen of FIG. 6.

The upper and lower platen temperatures were set at 127° C. A silicon release liner was placed below the polymer sample on the lower platen. A silicon release liner also was placed over the polymer sample. The platens were set to exert a pressure of 7,030 kilograms per square meter (kg/m$^2$). Upon achieving 7,030 kg/M$^2$, the pressure was released, then raised back to 7,030 kg/m$^2$ and maintained until the platen temperatures fell to about 35° C. The pressed films with release liners then were removed from the accessory. The resulting film samples had thicknesses of about 0.0127 cm, and were 25 cm in length and 20 cm wide.

Rectangular film samples were cut having a gauge length of 63.5 millimeters (mm) and a gauge width of 19.05 mm. Gauge thickness, as shown in Table II hereof, was measured with a STARRETT® #216 micrometer. A LIVECO® VITRODYNE® 1000 tensile tester with submersible jaws and facings (available from John Chatillon & Sons, 7609 Business Park Drive, Greensboro, N.C.) was used to measure peak tensile stress. Jaw separation speed was set at 3,000 micrometers per second. Jaw separation was set at 32,000 micrometers. Test options were set to Auto Return. Force limit was set to 100%. Cutoff frequency was set at 200 Hertz. All thickness and peak tensile stress values shown in Table II are averages, based upon at least n=4 measurements.

The first series of samples (Sample 1) was tested for peak tensile stress in a dry condition. That is, the Sample I films were not placed in or subjected to an aqueous solution or medium prior to testing.

The second series of samples (Sample 2) was tested for peak tensile stress after being submerged for one minute in 2,000 milliliters (ml) of Blood Bank Saline, 0.85% NaCl, Catalog No. B3158-1 (available from Baxter Healthcare Corp.).

The third series of samples (Sample 3) was tested for peak tensile stress after being submerged for one minute in 2,000 ml of Blood Bank Saline, 0.85% NaCl, Catalog No. B31581 with 1.0% sulfate anion added.

The fourth series of samples (Sample 4) was tested for peak tensile stress after being submerged for one minute in 2,000 ml of deionized water having a resistance greater than or equal to 18 megaohms.

The fifth series of samples (Sample 5) was tested for peak tensile stress after being submerged for thirty minutes in 2,000 ml of deionized water having a resistance greater than or equal to 18 megaohms.

The thickness and peak tensile stress data for Samples 1–7 were as follows:

TABLE II

| Sample No. | No. of Measurements | Thickness (micrometers) | Peak Tensile Stress (MPa) |
|---|---|---|---|
| 1 | 5 | 0.322 | 4.51 |
| 2 | 5 | 0.291 | 4.32 |
| 3 | 4 | 0.201 | 4.43 |
| 4 | 5 | 0.326 | 0.07 |
| 5 | 5 | 0.216 | 0.00 |

The peak tensile stress data shown herein illustrates that film samples formed of the National Starch 70-4442 copolyester polymer are significantly affected by the presence of the sulfate anion (a kosmotrope) in solution, which tends to build or increase tensile strength at high concentration levels, such as found in infant or adult urine. However, in the presence of excess water, in which the concentration of the sulfate anion is below the critical precipitation concentration (i.e., approximately 2000 parts per million), the copolyester polymer (or copolymer) precipitates from solution, weakening the film strength whereby the film tends to disperse.

EXAMPLE 4

In this example, film samples formed from National Starch 70-4442 polymer were tested for dispersion in deionized water as compared to commercially available bath tissue, substantially in accordance with "A Simple Test for Dispersion of Wet Chop Fiberglass in Water", published in the 1996 TAPPI Proceedings Nonwovens Conference and incorporated herein by reference. Five 1.5 inch (38.1 mm) long by 1.5 inch (38.1 mm) wide film samples (Sample 1) having an average weight of 0.2525 gram were placed in 1,500 ml of deionized water having a resistance greater than or equal to 18 megaohms contained in a 2,000 ml Kimax beaker, No. 14005. A Fisher Scientific Stirrer (Magnetic), Catalog No. 11-498-78H, was set at a speed setting of 7 to agitate the contents of the beaker. Using a standard timer, the period of time was measured from the point the stirrer was activated until the onset of dispersion occurred, which was defined as the point at which the first piece of sample film material broke off or away from the remaining portion of the film sample, and until full dispersion occurred, which was defined as the point at which the sample film material had dispersed into pieces having diameters not exceeding about 0.25 inch (6.35 mm).

Five single sheets of KLEENEX® Premium Bath Tissue (Sample 2) available from Kimberly-Clark Corp. of Dallas, Tex., each measuring 4.0 inches (10.2 cm) by 4.5 inches (11.4 cm) and having an average weight of 0.3274 gram, were subjected to the same test procedure and the periods for the onset of dispersion and full dispersion were measured.

Finally, this test procedure was repeated by placing a single 1.5 inch (38.1 mm) by 1.5 inch (38.1 mm) sample of film (Sample 3) made from National Starch 70-4442 polymer, having a weight of 0.2029 gram, in 1,500 ml of Blood Bank Saline, 0.85% NaCl, Catalog No. B3158-1 with 0.1% sulfate anion added. The periods for onset of dispersion and full dispersion were measured. As can be seen from Table III below, no dispersion occurred for a period of 15 minutes, at which time the test was terminated.

TABLE III

| Sample No. | No. of Measurements | Onset of Dispersion (seconds) | Full Dispersion (seconds) |
|---|---|---|---|
| 1 | 5 | 57.2 | 82.4 |
| 2 | 5 | 45.4 | 122.0 |
| 3 | 1 | None after 15 minutes | None after 15 minutes |

The results of the test procedures performed under this Example further illustrate that fibers employing the triggered, water-dispersible 70-4442 polymer, in accordance with the present invention, will disperse in the presence of a particular trigger component, such as the sulfate anion, at a concentration level found in excess water, while remain substantially unaffected when exposed to the same trigger component at a concentration level typically found in body fluids, such as infant or adult urine. Moreover, the rate of dispersion compares favorably to that of commercial bath tissue products, which generally are disposed of in normal tap water, such as is found in toilet bowls.

Having thus described the invention in detail, it should be apparent that various modifications and changes can be made in the present invention without departing from the spirit and scope of the following claims.

What is claimed is:

1. A multicomponent fiber comprising:
    a first component and at least a second component,
    said second component comprising a thermoplastic polymer,
    said first component forming an exposed surface on at least a portion of said fiber,
    said first component comprising a heat bondable polymer,
    said first component further comprising a water-dispersible polymer that remains stable in the presence of an aqueous solution having greater than about 1000 ppm of a kosmotrope and disperses in a period not exceeding 30 minutes in an aqueous solution having less than about 1000 ppm of a kosmotrope.

2. A multicomponent fiber according to claim 1 wherein said first component comprises water-dispersible polyester.

3. A multicomponent fiber according to claim 1 wherein said first component comprises water-dispersible polyamide.

4. A multicomponent fiber according to claim 2 wherein said first component comprises a water-dispersible copolyester.

5. A multicomponent fiber according to claim 1 wherein said first component disperses in a period not exceeding 15 minutes.

6. A multicomponent fiber comprising:
    a first component and at least a second component,
    said second component comprising a thermoplastic polymer,
    said first component forming an exposed surface on at least a portion of said fiber,
    said first component comprising a heat bondable polymer,
    said first component further comprising a water-dispersible polymer having a first peak tensile stress in the presence of an aqueous solution having greater than about 1000 ppm of a kosmotrope, and a second peak tensile stress in the presence of an aqueous solution having less than about 1000 ppm of a kosmotrope, said second peak tensile stress being at least 90% less than said first peak tensile stress.

7. A multicomponent fiber according to claim 6 wherein said first component comprises a water-dispersible copolyester.

8. A multicomponent fiber according to claim 6 wherein said second peak tensile stress is at least 95% less than said first peak tensile stress.

9. A nonwoven web comprising a plurality of fibers, at least a portion of said plurality of fibers comprising the multicomponent fibers of claim 1.

10. A personal care absorbent article which includes a nonwoven web according to claim 9.

11. A wiper including a nonwoven web according to claim 9.

12. A diaper including a nonwoven web according to claim 9.

13. A training pant including a nonwoven web according to claim 9.

14. An incontinence garment including a nonwoven web according to claim 9.

15. A sanitary napkin including a nonwoven web according to claim 9.

16. A panti-liner including a nonwoven web according to claim 9.

17. A bandage including a nonwoven web according to claim 9.

* * * * *